United States Patent [19]
Matsuda et al.

[11] 3,988,309
[45] Oct. 26, 1976

[54] EEL CALCITONIN

[75] Inventors: Tetsuo Matsuda; Susumu Watanabe, both of Shizuoka; Shunpei Sakakibara, Suita; Eisuke Munekata, Toyonaka; Tadanori Morikawa, Takatsuki; Masaru Otani, Shizuoka; Toshiharu Noda, Toyonaka; Hirose Yamauchi, Shizuoka; Tosio Meguro, Shizuoka; Shuichi Kitazawa, Shizuoka, all of Japan

[73] Assignee: Toyo Jozo Kabushiki Kaisha, Japan

[22] Filed: Dec. 17, 1974

[21] Appl. No.: 536,889

[30] Foreign Application Priority Data
Dec. 27, 1973  Japan .............................. 48-144250
July 17, 1974  Japan .............................. 49-81138

[52] U.S. Cl. .......................... 260/112.5 T; 424/177
[51] Int. Cl.² .................. C07C 103/52; C07G 7/00
[58] Field of Search .................. 260/112.5, 112.5 T

[56] References Cited
FOREIGN PATENTS OR APPLICATIONS
2,111,518  10/1971  Germany Primary Examiner—Lewis Gotts
Assistant Examiner—Reginald J. Sauyat
Attorney, Agent, or Firm—Young & Thompson

[57] ABSTRACT

A polypeptide having calcitonin activity of the formula

H—Cys—Ser—Asn—Leu—Ser—Thr—Cys—Val
—Leu—Gly—Lys—Leu—Ser—Gln—Glu—Leu
—His—Lys—Leu—Gln—Thr—Tyr—Pro—Arg
—Thr—Asp—Val—Gly—Ala—Gly—Thr—Pro—NH$_2$ and the salts thereof with pharmaceutically acceptable acids.

1 Claim, No Drawings

EEL CALCITONIN

This invention relates to a novel polypeptide of the formula,

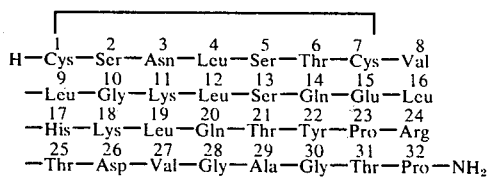

(I)

The above compound has serum calcium reducing activity in mammals, and can be generically called a calcitonin.

A hormone-like substance can be extracted from the tissue comprising vena cava attached to the esophagus near the heart of an eel of *genus Anguilla* and the pericardial membrane of an eel of *genus Anguilla* (refer to British Patent No. 1,342,812). The extraction and purification procedures of that patent, however, give extremely low yields and the purified substance of the present invention was never produced by that method.

We have recently found that the above polypeptide having serum calcium reducing property in mammals, which is thus a calcitonin, can be obtained as a pure substance with good yield by:

1. extracting the tissue using 40–70% (V/V) acidic aqueous organic solvent;
2. isolating the precipitated crude substance from the extract by adding sufficient water-immiscible organic solvent to precipitate the active substance; and
3. purifying the crude substance by a series of purification procedures comprising molecular sieve chromatography, and twice-performed ion-exchange chromatography using an acidic ion exchanger, and desalting.

We have also investigated the chemical structure of the eel calcitonin and determined it to be as follows:

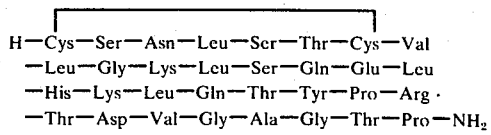

(I)

It is the object of the present invention to provide a novel polypeptide having serum calcium reducing property in mammals, that is, a so-called calcitonin.

The physico-chemical properties of the polypeptide of the present invention having serum calcium reducing activity in mammals are as follows:

1. Appearance of the product: white powder.
2. Solubility:
   soluble; water
   insoluble; non-polar solvents such as acetone, chloroform, ethylacetate, benzene, hexane and carbontetrachloride.
3. Molecular weight: 3414.73
4. Melting point: 220° C. (decomposed).
5. Primary structure:

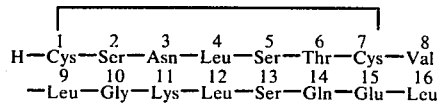
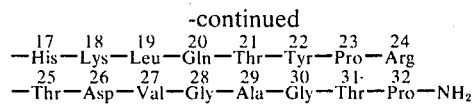

6. Rf value of thin layer chromatography:
   Rf = 0.65 – 0.71
   Carrier: cellulose
   Developer: n-butanol : pyridine : water : acetic acid (15 : 10 : 12 : 3)
   Coloring: Raydon-Smith reagent, ninhydrin.
7. Serum calcium reducing activity: 3700–6000 MRC u/mg. [Assay method]
   Sample is diluted adequately with 0.1 N sodium acetate – 0.1% albumin solution. Male rats are each subjected individually to intramuscular injection with 0.2 ml. of the dilution. After 1 hour, all the rats are killed to obtain their respective blood, and the serum calcium value of each blood sample is determined by atomic absorption spectrophotometry. On the other hand, Research Standard B, which is an extract obtained from thyroid gland of hog, is diluted so as to give dilutions of 2.5, 5, 10 and 20 MRC mu/0.2 ml. respectively. Male rats are each subjected to intramuscular injection with 0.2 ml. of the dilutions. Following the same procedure as above the serum calcium value of the rats is determined after 1 hour of injection. From the potency of the corresponding Research Standard, the potency of the calcitonin in the sample is determined.

It is already known that thyrocalcitonin as a mammalian serum calcium reducing polypeptide hormone had been extracted from thyroid gland of mammals or ultimobranchial body in birds and fishes. At present, the primary structures of hog, cattle, sheep, salmon and human calcitonins have been determined. These calcitonins are constructed from 32 amino acids, have the S—S bond between first and seventh amino acid from the amino group terminal, and have the proline amide group on the carboxyl group terminal. The other amino acid sequences are different from each other and hence the biological activities are different respectively, for example 50–200 MRC u/mg. for hog, cattle and human calcitonins and 25–50 times the activity thereof for salmon calcitonin.

The eel calcitonin of the present invention has a certain structural similarity to salmon calcitonin, the peptides of the first to 25th amino acid sequence being identical with each other, and the 26th to 32nd amino acid sequences thereof being different as follows:

|  | 26 | 27 | 28 | 29 | 30 | 31 | 32 |
|---|---|---|---|---|---|---|---|
| Product of the present invention | Asp | Val | Gly | Ala | Gly | Thr | Pro —NH$_2$ |
| Salmon calcitonin | Asn | Thr | Gly | Ser | Gly | Thr | Pro —NH$_2$ |

Therefore, the polypeptide of the present invention is a novel compound.

The eel calcitonin of the present invention has the same serum calcium and phosphorus reducing activity in mammals as known calcitonins, and therefore it may be a hormone which plays an important role in calcium metabolism.

Calcitonins inhibit absorption of the bone and intense interest has been shown toward their clinical use in metabolic osteopathy. The calcitonins are used at present clinically in the treatment of Paget's disease, osteoporosis and hypercalcemia.

A process for extraction of the calcitonin of the present invention is as follows:

As raw material, a portion of the tissue comprising vena cava attached to the esophagus near the heart of eel and/or the pericardial membrane of an eel are used. Particularly preferable is the portion of heart apart from the myocardium, or the portion of the tissue comprising vena cava attached to the esophagus near the heart of eel, or both. The tissue may be used in the form of defatted and dried product.

As extraction solvent, 40–70% (V/V) acidic aqueous organic solvent is used. Preferred examples are mixed solvents such as butanol : acetic acid : water (15 : 3 : 6–10) or butanol : pyridine : acetic acid : water (15 : 10 : 3 : 12).

Extraction can be performed by techniques that are known per se, and preferably at 50° C. for 24 hours.

To an aqueous extract was added a sufficient amount of water-miscible organic solvent to precipitate the active substance, i.e., polypeptide of molecular weight 3414. Examples of the water-miscible organic solvent may be lower alcohol, acetone and the like.

The precipitate is dissolved, in a diluted acid such as 0.2 N hydrochloric acid or 0.1 N formic acid. The supernatant solution is subjected to molecular sieve chromatography to separate the active substance and higher molecular weight miscellaneous proteins.

As the carrier, dextran gel such as Sephadex G-25, G-50 or G-75 or acrylamide such as Biogel P-10 may be used. A volatile acidic solution, such as low concentration formic acid or ammonium formate may be used as a developer.

The eluates thereof are collected and active fractions are separated by chromatography using an acidic ion-exchanger such as strongly or weakly acidic ion-exchange resin, cellulose ion-exchanger or cross-linked dextran ion-exchanger. Examples of the ion-exchanger are Amberlite IR-120, IR-50, Dowex 50, Duolite C-3, C-25, C-62 or CS-101, CM-cellulose, SE-cellulose, SP-sephadex, SE-sephadex or CM-sephadex. Elution can be effected using a volatile acidic buffer solution such as ammonium formate or ammonium acetate. The pH and concentration of the solution may be adjusted for elution. Active substance can be eluted over the range of 0.1 to 1 molar linear gradient elution at pH 2–6 for strongly acidic ion-exchangers, and 0.01 to 0.1 molar concentration of linear gradient elution at pH 4–6 for weakly acidic ion-exchangers.

Each eluate is checked by bio-assay and active fractions are desalted. Desalting can be conventionally effected by molecular sieve chromatography on dextran gel such as Sephadex G-25 or G-50 or acrylamide such as Biogel P-10, or by filtration through a membrane filter such as Amicon UM-2.

Further active fractions are collected and rechromatographed by using acidic ion-exchanger. Each eluate is again checked by bio-assay and active fractions are collected and desalted to obtain the pure active substance.

As hereinbefore described, the novel polypeptide having calcitonin activity is obtained in pure form.

The novel calcitonin of the present invention can also be obtained by chemical synthesis.

The synthesis can be effected by peptide synthesis steps that are known per se, that is to say, an amino acid and peptide of 2 to 4 amino acids are reacted by condensation in the order of the amino acid sequence of formula [I], and the disulfide bridge is bonded by oxidation of the mercapto group at the stage of construction of the peptide unit containing two L-cysteinyl units.

If desired, the product is changed to its acid addition salt or complex.

The protective groups in the synthesis of the starting materials or intermediates are conventional protective groups for peptide synthesis and are easily removed by hydrolysis, acid hydrolysis, reduction, aminolysis or hydrazinolysis. For example the amino group is protected conventionally by an acyl group such as formyl, an aralkyl group such as a triphenylmethyl group, a benzyloxycarbonyl group such as a p-methoxy benzyloxy carbonyl group, an aliphatic oxycarbonyl group such as a t-butoxycarbonyl group or an enamin type group. The carboxyl group can be protected by its amide formation, hydrazide formation or esterification. The hydroxy group in serine, threonine or tyrosine may optionally be protected by esterification or etherification.

The mercapto group is cysteine, the amino group in the guanidino group of arginine, and the imino group in histidine may be protected by acylation or alkylation, a nitro or tosyl group, and a trityl or benzyl group, respectively.

The peptides of the starting material or intermediates are synthesized by condensation of amino acids or a peptide of two to four amino acids in the order of the amino acid sequence of formula [I], and the peptide containing two L-cysteinyl groups is produced by constructing a disulfide bond in the stage of its peptide construction. For example, an amino acid or peptide having a protected α-amino group and an activated terminal carboxyl group is reacted with an amino acid or peptide having a free α-amino group and a protected terminal carboxyl group. On the other hand, an amino acid or peptide having an activated α-amino group and a protected terminal carboxyl group is reacted with an amino acid or peptide having a free terminal carboxyl group and a protected α-amino group.

The carboxyl group hereinabove can be activated by a conventional technique such as by acid azide, acid anhydride, active ester or carbodiimide.

The preferred condensation reactions are the carbodiimide, azide, active ester or anhydride methods. In the condensation reaction, racemization should be carefully avoided.

The disulfide bond in the novel peptide of the present invention may cleave in any of various stages of the reaction process, and therefore it should preferably be constructed as late as possible in the synthesis. Accordingly, disulfide bond formation may preferably be effected by the reaction of the peptide, without containing a cysteinyl group such as protected docosa-peptideamide (No. 11-32), with another peptide containing a cysteinyl group such as protected deca-peptide (No. 1-10). The disulfide bond formation is effected by oxidizing the protected peptide having a free mercapto group, with iodine in glacial acetic acid, ethane diiodide in an organic solvent or oxygen in pH 6.5 water or hydrogen peroxide. The mercapto group protected for example by a trityl or acetamide group can be bonded simultaneously removing the said protective group by treatment with iodine in methanol.

The novel polypeptide [I] of the present invention can be obtained in the form of the free base or salt thereof. The free base may conventionally be obtained from its salt. The free base can be changed to its pharmaceutically acceptable salt by reacting with a pharmaceutically acceptable inorganic or organic acid such as hydrochloric, phosphoric, citric or the like.

The novel polypeptide hereinabove can be complexed by addition of inorganic or organic substances. The complex has long term activity when administered. Examples of the complex forming substances are inorganic compounds derived from metal such as calcium, magnesium or zinc, especially the phosphates, pyrophosphates or polyphosphates of the said metals. Examples of complex forming organic substance are non-antigenic gelatine, CMC, polyglutamic acid or the like.

The abbreviations in this specification have the following meanings:

BOC: t-butoxycarbonyl,
AOC: t-amyloxycarbonyl,
DIP: diisopropylmethoxycarbonyl,
Cbz: benzyloxycarbonyl,
Bzl: benzyl,
Mbzl: p-methoxybenzyl,
Tos: tosyl,
OEt: ethyl ester,
OBzl: benzyl ester,
ONP: p-nitrobenzyl ester,
OSU: N-hydroxysuccinylimide ester,
Cys: L-cysteine
Ser: L-serine,
Asn: L-asparagine,
Leu: L-leucine,
Thr: L-threonine,
Val: L-valine,
Gly: glycine,
Lys: L-lysine,
Gln: L-glutamine,
Glu: L-glutamic acid,
His: L-histidine,
Tyr: L-tyrosine,
Pro: L-proline,
Arg: L-arginene,
Asp: L-aspartic acid,
Ala: L-alanine,
TFA: trifluoroacetic acid,
TosOH: p-toluenesulfonic acid,
CHA: cyclohexylamine,
DCHA: dicyclohexylamine,
THF: tetrahydrofuran,
DMF: dimethylformamide,
DCC: dicyclohexylcarbodiimide,
WSC: N-ethyl-N'-dimethylaminopropyl-carbodiimide,
HOBT: 1-hydroxybenzotriazole,
MeOH: methanol,
EtOH: ethanol,
AcOH: acetic acid.

Following examples illustrate the present invention but not construed as limiting.

EXAMPLE 1

A. Preparation of raw material for extraction 3 kg. of tissue comprising vena cava attached to esophagus near the heart and pericardial membrane of the heart of eels was dehydrated three times by repeating the step of immersing the tissue and pericardial membrane in 30 l. of acetone containing 0.6 g. of EDTA at 5° C. for 5 hours. Immersing the dehydrated tissue and pericardial membrane in 15 l. of chloroform at 5° C. for 2 hours was repeated two times. The same dehydrating step as above but using 15 l. of acetone was repeated three times. The resulting precipitate was air-dried to obtain 820 g. of dried product (20 MRC mu/mg.)

B. Extraction 1.4 kg. of the thus-obtained dried product was suspended in a mixed solvent comprising 7.5 l. of butanol, 1.5 l. of acetic acid and 5 l. of water and stirred at 50° C. for 24 hours. Further 5 l. of butanol and one liter of acetic acid was added thereto, and stirred at 50° C. for 1 hour. The mixture was centrifuged (3000 r.p.m.) to obtain supernatant. To the precipitate were further added 7.5 l. of butanol, 1.5 l. of acetic acid and 3 l. of water, stirred at 50° C. for 1 hour and the supernatant obtained by centrifuge (3000 r.p.m.) was combined with the supernatant hereinabove. The combined supernatant was concentrated in vacuo up to 1/5 volume thereof and the precipitate formed was centrifuged off.

To the supernatant clear liquid was added five times its volume of acetone, allowed to stand overnight at 5° C. and the thus-formed precipitate was recovered by centrifugal separation and washed with acetone to obtain 65 g. of active powder (300 MRC mu/mg.)

65 g. of the active powder were homogenized with 1.4 l. of 0.2 N HCl and centrifuged (1600 r.p.m.) to obtain supernatant. The precipitate was again washed with one liter of 0.2 N HCl and the supernatant was combined with the former supernatant to obtain 2.2 l. of HCl solution of the active substance (8.8 MRC u/ml.).

C. Purification

To 200 ml. of hydrochloric acid solution containing active substance was added 96 g. of urea. The solution was passed through a column (10 cm. × 1 m.) packed with Sephadex G-25 buffered with 0.1 N formic acid solution and eluted with 0.1 N formic acid at a flow rate of 180 ml./hr. for molecular sieve chromatography. The eluate was collected in fractions of 20 ml. each. The active fractions detected by bio-assay (fractions Nos. 270–330) were collected and freeze dried to obtain 45 mg. of active powder (25 MRC u/mg.)

Subsequently, 4 g. of the active powder were dissolved in 100 ml. of 0.1 molar ammonium formate solution (pH 3.4). The solution was passed through a column (7.5 × 50 cm.) packed with SP-Sephadex C-25 buffered with the same aqueous ammonium formate and gradiently eluted at a flow rate of 500 ml./hr. each with 40 l. of 0.1–0.7 molar ammonium formate (pH 3.4). The resulting eluate was collected in fractions of 400 ml. each. The active fractions detected by bio-assay (fractions Nos. 150–200) were gathered. The gathered fractions were concentrated by membrane filtration (Amicon UM-2) and freeze dried to obtain 250 mg. of active powder (200 MRC u/mg.)

60 mg. of the active powder were dissolved in 1 ml. of 0.1 molar ammonium formate solution containing 480 mg. of urea. The solution was passed through a column (1.2 × 250 cm.) packed with Sephadex G-50 buffered with the said ammonium formate, and eluted with 0.1 N formic acid solution at a flow rate of 5 ml./hr. Each 4 ml. fraction of the eluate was collected and checked by bio-assay. The active fractions (fractions Nos. 70–83) were collected and freeze dried to obtain 23 mg. of active powder (400 MRC u/mg.)

90 mg. of the active powder were dissolved in 10 ml. of water adjusted with hydrochloric acid to pH 4.37 and charged on a column (1.2 × 35 cm.) packed with CM-cellulose equilibrated with 0.01 molar ammonium acetate (pH 4.37). The column was washed with one liter of 0.01 molar ammonium acetate (pH 4.37), then 2 l. of 0.01 molar ammonium formate (pH 4.37), and thereafter gradiently eluted with each 2.5 l. of ammonium formate solution [0.01 molar (pH 4.37) – 0.07 molar (pH 6.0)] at a flow rate of 35 ml./hr. The eluate was collected in fractions of 20 ml. each and the active fractions gathered (Nos. 108–125) and freeze dried to obtain 9 mg. of active powder (2000 MRC u/mg.)

The 9 mg. of the active powder were dissolved in 1 ml. of 0.1 N formic acid solution, and finally passed through a column packed with Sephadex G-50 (1.2 cm. × 250 cm.), and eluted with 0.1 N formic acid solution at flow rate 5 ml./hr. Each 4 ml. fraction was collected and the active fractions were detected by bio-assay (fractions Nos. 71–77) and freeze dried to obtain 3 mg. of active powder (4000 MRC u/mg.)

The thus-obtained active powder is shown to be a single substance by thin layer chromatography, dics-electrophoresis and N-terminal analysis.

Amino acids analysis of this substance is as follows:
Analytical method:

20 γ of the powder were hydrolyzed with 6 N HCl at 105° C. for 24 hours. After desalting, the solids were dissolved in 1.2 ml. of 0.2 N citrate buffer (pH 3.25) and 1 ml. thereof was provided for analysis.

| Amino acid | n mol. | Amino acid | n mol. |
| --- | --- | --- | --- |
| Lys | 7.67 | Pro | 6.78 |
| His | 3.10 | Gly | 12.55 |
| Arg | 3.58 | Ala | 6.20 |
| Asp | 7.28 | Cys | (7.57)* |
| Thr | 11.45 | Val | 5.84 |
| Ser | 9.06 | Leu | 16.69 |
| Glu | 10.74 | Tyr | 2.45 |

*Determined as 7.57 n mole of cysteinic acid by amino acid analysis after performic acid oxidation.

EXAMPLE 2

720 mg. of BOC—Lys (DIP)—Leu—Ser(Bzl)—Gln—Glu(OBzl)—Leu—His—Lys(DIP)—Leu—Gln—Thr(Bzl)—Tyr(Bzl)—Pro—Arg(Tos)—Thr(Bzl)—Asp(OBzl)—Val—Gly—Ala—Gly—Thr(Bzl)—Pro—NH₂
was dissolved in 5 ml. of TFA at −5° C. After stirring for 35 minutes at room temperature, the solution was concentrated in vacuo and ethyl ether was added thereto to bring down a precipitate. The precipitate was dried over sodium hydroxide. The dried precipitate was dissolved in 1 ml. of DMF. To that solution was added 30 ml. of HOBT, 45 mg. of DCC and 220 mg. of

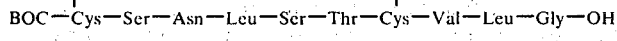
BOC—Cys—Ser—Asn—Leu—Ser—Thr—Cys—Val—Leu—Gly—OH at −5° C. and the mixture was stirred for 2 hours at 0° C. and overnight at room temperature. To the reaction mixture was added water. The thus-formed precipitate was collected by filtration, washed thoroughly with water and ethyl acetate, then dried in vacuo to obtain 740 mg. of crude product.

640 mg. of this crude material were treated with hydrogen fluoride at 20° C. for 1 hour in the presence of 3 g. of phenol and 2.5 ml. of anisole. After distillation of hydrogen fluoride, the residue was dissolved in 200 ml. of 0.5 molar acetic acid. The solution was washed with 150 ml. of ethyl acetate and passed through a column (2 × 20 cm.) of Dowex 1 × 2 (acetate form) and the eluate was freeze dried to obtain 590 mg. of the powder.

500 mg. of this powder were dissolved in 50 ml. of water adjusted with HCl to pH 4.37, and the said solution was charged on a column (2.0 cm. × 63 cm.) packed with carboxymethyl cellulose by 0.01 molar ammonium acetate (pH 4.37), then washed with 4 l. of 0.01 molar acetate buffer (pH 4.37) and 8 l. of 0.01 molar ammonium formate (pH 4.37). Thereafter the column was gradiently eluted with 12 l. of ammonium formate [0.01 molar (pH 4.37) – 0.07 molar (pH 6.0)]. The eluate was collected in fractions of 100 ml. each and the active fractions as detected by bio-assay were gathered and freeze dried to obtain the active powder.

50 mg. of this active powder was dissolved in 5 ml. of 0.1 N formic acid, passed through a column (1.2 cm. × 250 cm.) of Sephadex G-50, and eluted with 0.1 N formic acid at a flow rate of 10 ml./hr. The active fractions were collected and freeze dried to obtain the product, characterized as follows:

Melting point: 220° C. (decomposed).
$[\alpha]_D^{20} = -75°$ (c=1, 0.1 N-HCOOH).
Potency = 4000 MRC u/mg.
Amino acid composition: Cys/2 2.13 (2), Ser 2.86 (3), Leu 5.10 (5), Thr 3.48 (4), Val 2.20 (2), Gly 3.00 (3), Lys 1.98 (2), Glu 3.27 (3), His 0.95 (1), Tyr 0.90 (1), Pro 1.96 (2), Arg 1.03 (1), Asp 2.07 (2), Ala 0.94 (1)
Rf value = 0.65 – 0.71,
carrier: cellulose,
developer: n-BuOH — pyridine — AcOH — water (15 : 10 : 3 : 12)

Having described our invention, we claim:
1. A polypeptide selected from the group consisting of a compound of the formula

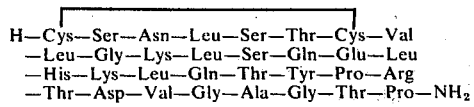
H—Cys—Ser—Asn—Leu—Ser—Thr—Cys—Val
—Leu—Gly—Lys—Leu—Ser—Gln—Glu—Leu
—His—Lys—Leu—Gln—Thr—Tyr—Pro—Arg
—Thr—Asp—Val—Gly—Ala—Gly—Thr—Pro—NH₂ and salts thereof with pharmaceutically acceptable acids.

* * * * *